United States Patent [19]

Curran

[11] 4,334,062

[45] Jun. 8, 1982

[54] CEPHALOSPORANIC ACID DERIVATIVES

[75] Inventor: William V. Curran, Pearl River, N.Y.

[73] Assignee: American Cyanamid Company, Stamford, Conn.

[21] Appl. No.: 200,236

[22] Filed: Oct. 24, 1980

[51] Int. Cl.$^3$ .............................................. C07D 501/18
[52] U.S. Cl. .................................... 544/026; 424/246; 544/27
[58] Field of Search ........................ 544/30, 26, 28, 27, 544/21; 424/246

[56] References Cited

U.S. PATENT DOCUMENTS

| 4,064,122 | 12/1977 | Ishimaru et al. | 544/26 |
| 4,113,944 | 9/1978 | Kai et al. | 544/26 |
| 4,183,925 | 1/1980 | Baxter et al. | 544/26 |

FOREIGN PATENT DOCUMENTS

| 859384 | 10/1977 | Belgium . |
| 78/1433 | 2/1978 | South Africa . |
| 78/01870 | 3/1978 | South Africa . |

Primary Examiner—Nicholas S. Rizzo

Attorney, Agent, or Firm—Richard J. Hammond; Barbara A. Shimei

[57] ABSTRACT

7-Acetamidocephalosporins are disclosed herein which are substituted at position 3 of the cephalosporin nucleus with the group

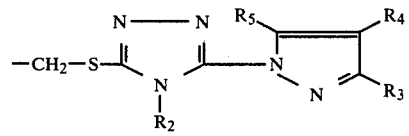

wherein $R_2$ is selected from the group hydrogen, amino, $C_1$ to $C_6$ alkylamino and di-$C_1$ to $C_6$ alkylamino and $R_3$, $R_4$ and $R_5$ are the same or different and are selected from the group hydrogen, hydroxy, $C_1$ to $C_6$ alkyl, $C_1$ to $C_6$ alkoxy, trifluoromethyl, phenyl, substituted phenyl, heterocyclic aryl and $R_3$ and $R_4$ or $R_4$ and $R_5$ taken together are the moiety —$CH_2(CH_2)_2CH_2$—, and the pharmaceutically acceptable non-toxic salts thereof.

4 Claims, No Drawings

CEPHALOSPORANIC ACID DERIVATIVES

FIELD OF THE INVENTION

This invention is related to cephalosporanic acids, esters, amides and acid salts. More particularly, this invention is related to such cephalosporanic compounds having at the 3 position the group —CH₂—S— heterocyclic aryl.

DISCUSSION OF THE PRIOR ART

The prior art discloses a variety of cephalosporin compounds bearing at position 3 of the cephalosporin nucleus a —S— hetero group. For example, 3—S—heterocyclic cephalosporins have been studied where the 7-acyl side chain is substituted with benzyl or thienylmethyl, the heterocyclic moiety being the tetrazole, thiadiazole, or triazole type. See Irish Pat. No. 415/62; Derwent Basic No. 7,044 and Van Heyningen, E., (1967), *Advan. Drug Res.* 4, 1–70.

The subject is reviewed in the book "Structure-activity Relationships Among the Semisynthetic Antibiotics", edited by D. Perlman; the chapter by Weber and Ott, part G with its accompanying tables. However, 3-S-heterocyclics bearing a pyrazolyl-substituted 1,2,4-triazole have not been synthesized.

SUMMARY OF THE INVENTION

This invention is concerned with 3-S-heterocephalosporins of the formula

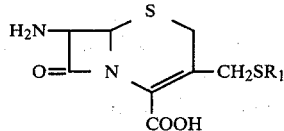

wherein $R_1$ is a moiety selected from the group of the formula

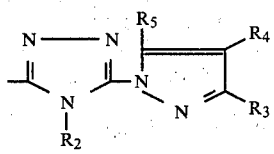

wherein $R_2$ is selected from the group hydrogen, amino, $C_1$ to $C_6$ alkylamino and di-$C_1$ to $C_6$ alkylamino; $R_3$, $R_4$ and $R_5$ are the same or different and are selected from the group hydrogen, hydroxy, $C_1$ to $C_6$ alkyl, $C_1$ to $C_6$ alkoxy, trifluromethyl, phenyl substituted phenyl, heterocyclic aryl and $R_3$ and $R_4$ or $R_4$ and $R_5$ taken together are the moiety —CH₂(CH₂)₂CH₂—; and the pharmaceutically acceptable non-toxic salts thereof. The compounds are antibacterial agents active against Gram positive and negative bacteria.

The present invention further encompasses the process for the preparation of the compounds of formula I.

DESCRIPTION OF THE PREFERRED EMBODIMENTS

The compounds of the present invention are generically represented by the following:

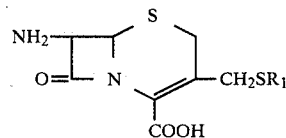

wherein $R_1$ is a moiety selected from the group of the formula

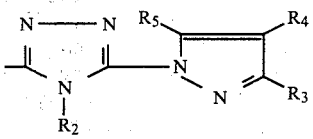

wherein $R_2$ is selected from the group hydrogen, amino, $C_1$ to $C_6$ alkylamino, and di-$C_1$ to $C_6$ alkylamino; $R_3$, $R_4$ and $R_5$ are the same or different and are selected from the group hydrogen, hydroxy, $C_1$ to $C_6$ alkyl, $C_1$ to $C_6$ alkoxy, trifluoromethyl, phenyl, substituted phenyl, heterocyclic aryl, and $R_3$ and $R_4$ or $R_4$ and $R_5$ taken together are the moiety —CH₂(CH₂)₂CH₂—; $R_7$ is $C_1$ to $C_6$ alkoxy and the pharmaceutically acceptable salts thereof.

In the compounds of formula I, it is preferred that $R_3$, $R_4$ and $R_5$ are the same or different and are selected from the group hydrogen; $C_1$ to $C_3$ alkyl, for example methyl, ethyl, n-propyl or i-propyl; phenyl; phenyl substituted with mono or di methyl, methoxy, chloro, bromo or trifluoromethyl, thienyl, and pyrroyl.

In the above preferred compounds when $R_3$, $R_4$ and $R_5$ are the same and are hydrogen, it is preferred that $R_2$ is selected from the group hydrogen and amino, most preferably amino.

In the above preferred compounds, when $R_3$, $R_4$ and $R_5$ are different, it is most preferred that such are selected from the group (on the pyrazol-1-yl nucleus) hydrogen, 3-methyl, 3-phenyl, 3-thien-2-yl, 3,5-dimethyl, 3-methyl-5-phenyl and 3-methyl-5-thien-2-yl. In such preferred and most preferred compounds, it is preferred that $R_2$ is selected from the group hydrogen and amino, most preferably amino.

Particularly preferred are the following compounds: 7-amino-3-[[4-amino-5-(3,5-dimethyl-1-pyrazolyl)-4H-1,2,4-triazol-3-ylthio]methyl]-8-oxo-5-thia-1-azabicyclo[4.2.0]oct-2-ene-2-carboxylic acid; 7-amino-3-[[4-amino-5-(3-methyl-5-phenyl-1-pyrazolyl)-4H-1,2,4-triazol-3-ylthio]methyl]-8-oxo-5-thia-1-azabicyclo[4.2.0]oct-2-ene-2-carboxylic acid; and 7-amino-3-[[4-amino-5-(1-pyrazolyl)-4H-1,2,4-triazol-3-ylthio]methyl]-8-oxo-5-thia-1-azabicyclo[4.2.0]oct-2-ene-2-carboxylic acid.

The compounds of the present invention may be prepared as indicated by the following diagram and description:

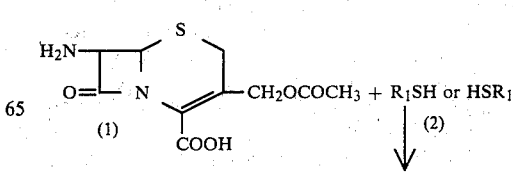

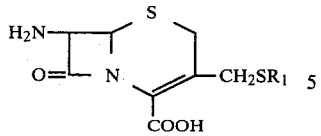

where $R_1$ is as previously defined.

7-Aminocephalosporanic acid (1) is reacted with an appropriate mercapto-pyrazolyltriazole (2) where $R_1$ is as previously defined, in aqueous organic or inorganic base, e.g., sodium bicarbonate with sufficient solvent to produce solution, for a time and temperature sufficient to effect the desired reaction, typically about 50°-70° for 6 to 12 hours. While any of a variety of inert solvents may be used, the solvents of preference are those polar solvents such as acetone water as mixtures thereof. The amount of organic or inorganic base present in the reaction varies depending on the base strength of the actual base used. Sufficient base to effect the coupling reaction will be achieved at a pH of from about 6 to about 8 most preferably pH 6.4, typically using phosphate buffer containing sodium bicarbonate. The reaction mixture is then acidified with a suitable mineral acid such as dilute hydrochloric acid and the product cephalosporin of formula I separated by convention techniques. Such techniques include extraction of the reaction solution with a suitable organic solvent, precipitating the product by chilling or various chromatographic techniques such as exemplified by the column, thin layer or paper chromatographic procedures.

As an alternate embodiment, the compounds of formula I are obtained by reacting compound (1) with the appropriate mercapto pyrazolyltriazole (2) in a polar solvent such as acetonitrile at 100°-200° C. for about 10 to about 40 hours. The solution is typically evaporated to obtain the product.

In the specification herein the term "$C_1$ to $C_6$ alkyl" is intended to mean those fully saturated monovalent radicals containing only carbon and hydrogen, such including both branched and linear aliphatic carbon chains of not more than 6 carbon atoms. Examples of such alkyl groups include methyl, ethyl, n-propyl, i-propyl, t-butyl, etc. The term "substituted phenyl" includes both mono and disubstituents on the phenyl group such as for example, $C_1$ to $C_3$ alkyl, $C_1$ to $C_3$ alkoxy, halo (fluoro, chloro and bromo), trifluoromethyl, etc. The term "heterocyclic aryl" includes the substituted and unsubstituted aromatic ring compounds of five or six members composed principally of carbon but including in such ring one, two or three members other than carbon such as nitrogen, oxygen, sulfur or mixtures thereof. Such hetero groups include 2- or 3-pyrroyl, 2 or 3-furyl, 2,4 or 5-oxazolyl, 3,4 or 5-isothiazolyl, 1,3,4-triazol-2-yl etc. Substituents include those disclosed before for the term "substituted phenyl".

The compounds of the present invention are active antibacterial agents.

They are also useful as intermediates for the preparation of other semi-synthetic cephalosporin derivatives, as disclosed in copending Application Ser. No. 145,071, filed Apr. 30, 1980, incorporated herein by reference.

A further understanding of the invention can be had from the following non-limiting preparations and examples. As used herein above and below, unless expressly stated to the contrary, all temperatures and temperature ranges refer to the centigrade system and the terms ambient or room temperature refer to about 20° C. The term percent or (%) refers to weight percent and the term mole and moles refers to gram moles. The term equivalent refers to a quantity of reagent equal in moles to the moles of the preceding or succeeding reactant recited in that preparation or example, in terms of moles of finite weight or volume.

EXAMPLE 1

7-Amino-3-[[4-amino-5-(1-pyrazolyl)-4H-1,2,4-triazol-3-ylthio]methyl]-8-oxo-5-thia-1-azabicyclo-[4.2.0]oct-2-ene-2-carboxylic acid A solution of 2.72 g. of 7-aminocephalosporanic acid, 1.82 g. of 4-amino-5-(1-pyrazolyl)-4H-1,2,4-triazole-3-thiol and 1.68 g. of sodium bicarbonate in 75 ml. of pH 6.4 phosphate buffer is stirred and heated at 60° C. for 7 hours. The resulting solution is cooled, acidified to pH 3 with 4 N hydrochloric acid and the precipitate is collected by filtration and dried, giving 2.6 g. of the desired product, I.R. 5.60μ (β-lactam carbonyl).

EXAMPLE 2

7-Amino-3-[[4-amino-5-(3,5-dimethyl-1-pyrazolyl)-4H-1,2,4-triazol-3-ylthio]methyl]-8-oxo-5-thia-1-azabicyclo[4.2.0]oct-2-ene-2-carboxylic acid A 1.36 g. portion of 7-aminocephalosporanic acid, 1.05 g. of 4-amino-5-(3,5-dimethyl-1-pyrazolyl)-4H-1,2,4-triazole-3-thiol and 0.84 g. of sodium bicarbonate are reacted by the procedure of Example 1, giving the desired product, I.R. 5.60μ (β-lactam carbonyl).

EXAMPLE 3

7-Amino-3-[[4-amino-5-(3-methyl-5-phenyl-1-pyrazolyl)-4H-1,2,4-triazol-3-ylthio]methyl]-8-oxo-5-thia-1-azabicyclo[4.2.0]oct-2-ene-2-carboxylic acid A mixture of 1.36 g. of 7-aminocephalosporanic acid, 1.50 g. of 4-amino-5-(3-methyl-5-phenyl-1-pyrazolyl)-4H-1,2,4-triazole-3-thiol and 0.84 g. of sodium bicarbonate in 40 ml. of pH 6.4 phosphate buffer is stirred and heated at 60° C. for 8 hours. The mixture is cooled to room temperature, filtered and the filtrate is extracted with ethyl acetate. The aqueous portion is acidified to pH 2.5 with 4 N hydrochloric acid. The precipitate is collected by filtration and dried, giving 0.8 g. of the desired product, I.R. 5.60μ (β-lactam carbonyl).

I claim:

1. A compound selected from those of the formula:

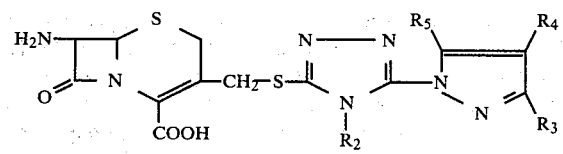

wherein
$R_2$ is selected from the group hydrogen, amino, $C_1$ to $C_6$ alkylamino and di-$C_1$ to $C_6$-alkylamino;
$R_3$, $R_4$, and $R_5$ are the same or different and are selected from the group hydrogen, hydroxy, $C_1$ to $C_6$ alkyl, $C_1$ to $C_6$ alkoxy, trifluoromethyl, phenyl, substituted phenyl, heterocyclic aryl, and $R_3$ and $R_4$ or $R_4$ and $R_5$ taken together are the moiety —$CH_2$—$(CH_2)_2$—$CH_2$—;
wherein the substituents on the phenyl are mono- or di-substituents which are the same or different and which are selected from the group $C_1$ to $C_3$ alkyl, $C_1$ to $C_3$ alkoxy, fluoro, chloro, bromo, and trifluoromethyl; and wherein the heterocyclic aryl is selected from the group of five- and six-membered aromatic ring compounds containing one to three heteroatoms which are the same or different and which are selected from the group oxygen, nitrogen, and sulfur, and wherein said heterocyclic aryl is optionally substituted as defined above for substituted phenyl;

and the pharmaceutically acceptable non-toxic salts thereof.

2. The compound 7-amino-3-[[4-amino-5-(1-pyrazolyl)-4H-1,2,4-triazol-3-ylthio]methyl]-8-oxo-5-thia-1-azabicyclo[4.2.0]oct-2-ene-2-carboxylic acid.

3. The compound 7-amino-3-[[4-amino-5-(3,5-dimethyl-1-pyrazolyl)-4H-1,2,4-triazol-3-ylthio]methyl]-8-oxo-5-thia-1-aziabicyclo[4.2.0]oct-2-ene-2-carboxylic acid.

4. The compound 7-amino-3-[[4-amino-5-(3-methyl-5-phenyl-1-pyrazolyl)-4H-1,2,4-triazol-3-ylthio]-methyl]-8-oxo-5-thia-1-azabicyclo[4.2.0]oct-2-ene-2-carboxylic acid.

* * * * *